(12) United States Patent
Kessler et al.

(10) Patent No.: US 9,395,350 B2
(45) Date of Patent: *Jul. 19, 2016

(54) GEM TESTER

(71) Applicant: Sy Kessler Sales, Inc., Dallas, TX (US)

(72) Inventors: Daniel L. Kessler, Dallas, TX (US); Henry M. Kessler, Dallas, TX (US)

(73) Assignee: Sy Kessler Sales, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/339,151

(22) Filed: Jul. 23, 2014

(65) Prior Publication Data

US 2014/0337035 A1   Nov. 13, 2014

Related U.S. Application Data

(63) Continuation-in-part of application No. 14/301,045, filed on Jun. 10, 2014, now Pat. No. 9,134,263, which is a continuation of application No. 14/058,343, filed on Oct. 21, 2013, now Pat. No. 8,749,253, which is a continuation of application No. 13/165,053, filed on Jun. 21, 2011, now Pat. No. 8,564,316.

(60) Provisional application No. 61/356,943, filed on Jun. 21, 2010, provisional application No. 61/946,521, filed on Feb. 28, 2014.

(51) Int. Cl.
*G01R 27/08*  (2006.01)
*G01N 33/38*  (2006.01)
*G01N 27/04*  (2006.01)
*G01N 25/18*  (2006.01)
*G10L 21/00*  (2013.01)
*G01N 33/24*  (2006.01)

(52) U.S. Cl.
CPC .............. *G01N 33/381* (2013.01); *G01N 25/18* (2013.01); *G01N 27/041* (2013.01); *G10L 21/00* (2013.01); *G01N 33/24* (2013.01)

(58) Field of Classification Search
CPC ....... G01N 25/18; G01N 27/02; G01N 27/04; G01N 27/041; G01N 33/24; G01N 33/381; G01N 2291/0232
USPC ........ 324/71.1, 693, 691, 649, 600, 713, 715, 324/717, 722, 724
See application file for complete search history.

(56) References Cited

U.S. PATENT DOCUMENTS

| | | |
|---|---|---|
| 2,789,430 A | 4/1957 | Sinclaire |
| 4,255,962 A | 3/1981 | Ashman |
| 4,344,315 A | 8/1982 | Moxon et al. |
| 4,364,677 A | 12/1982 | Ashman |
| 4,394,580 A | 7/1983 | Gielisse |

(Continued)

*Primary Examiner* — Hoai-An D Nguyen
(74) *Attorney, Agent, or Firm* — Scott T. Griggs; Griggs Bergen LLP

(57) ABSTRACT

A gem tester for testing a gem under test and a kit including a horizontal recharging stand are disclosed. In one embodiment of the gem tester, an elongated body has a line-of-sight contour tapering from a bulbous end to a radially deviating frontal nose having a probe extending therefrom. Internal circuitry measures electrical conductivity of the gem under test in order to identify the type of gem under test and drive a color control signal in response thereto. A light source is disposed proximate the probe in order to expose the gem under test to ultraviolet light prior to the internal circuitry measuring electrical conductivity. Identification of the gem under test may be made by audio or visual indication or a combination thereof.

20 Claims, 5 Drawing Sheets

(56) References Cited

U.S. PATENT DOCUMENTS

| | | |
|---|---|---|
| 4,488,821 A | 12/1984 | Wenckus |
| 5,801,819 A | 9/1998 | Spear et al. |
| 5,883,389 A | 3/1999 | Spear et al. |
| 5,955,735 A | 9/1999 | Coleman |
| 6,265,884 B1 | 7/2001 | Menashi et al. |
| 6,439,766 B1 | 8/2002 | Nelson |
| 7,126,351 B2 | 10/2006 | Claus |
| 7,259,839 B2 | 8/2007 | Sivovolenko |
| 7,362,109 B2 | 4/2008 | Loginov |
| 7,382,445 B2 * | 6/2008 | Sasian ............... G01N 21/8806 356/30 |
| 8,278,906 B2 | 10/2012 | Loginov et al. |
| 8,564,316 B2 | 10/2013 | Kessler et al. |
| 8,749,253 B2 | 6/2014 | Kessler et al. |
| 2012/0007619 A1 | 1/2012 | Zhu et al. |
| 2012/0059619 A1 * | 3/2012 | Zhu ....................... G01N 25/18 702/136 |

* cited by examiner

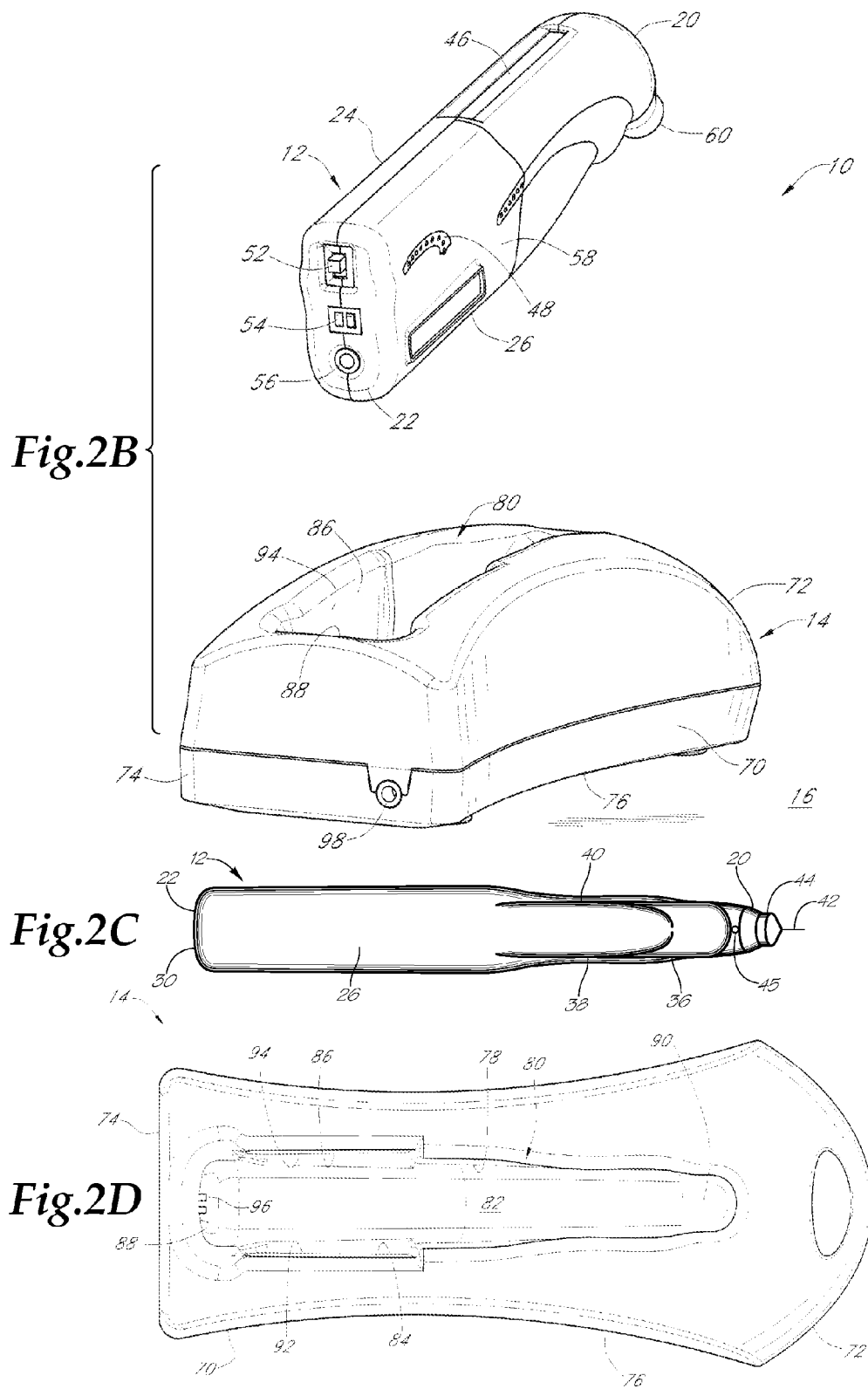

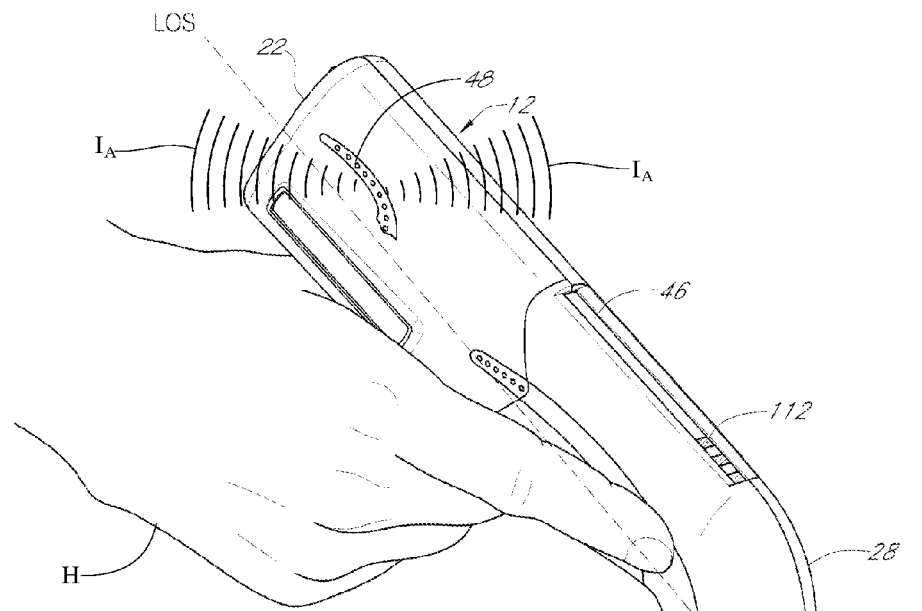
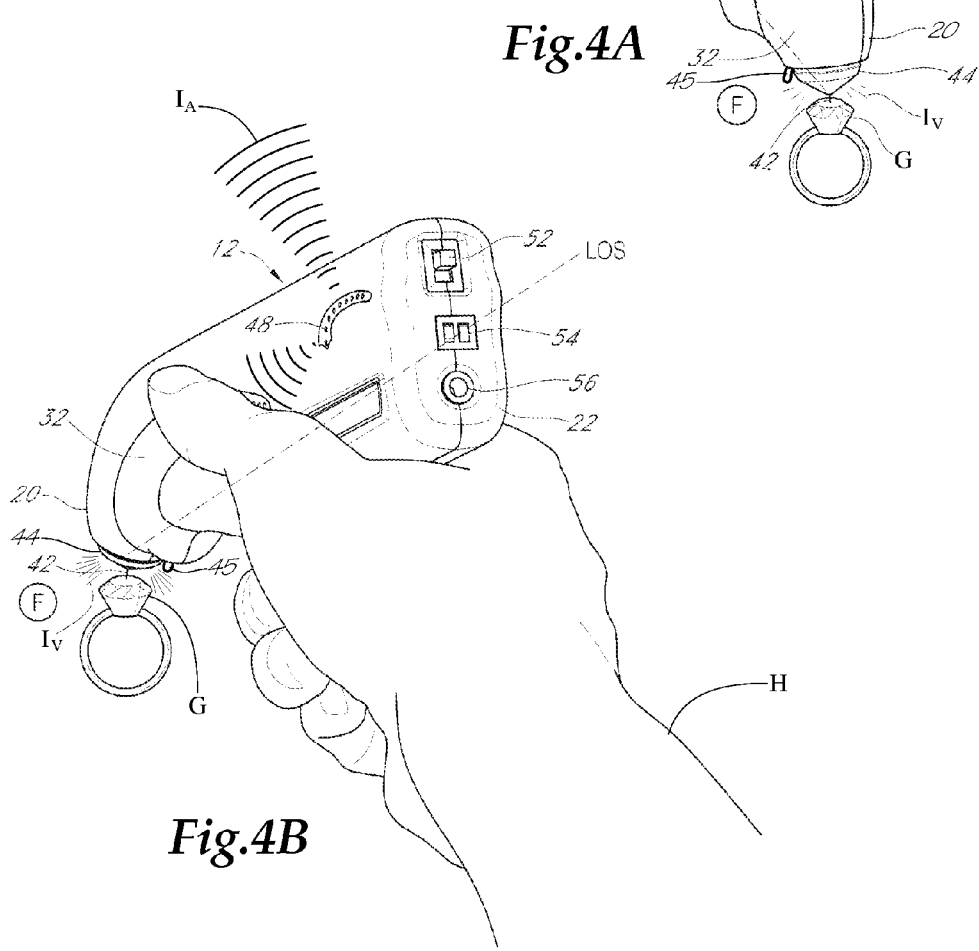

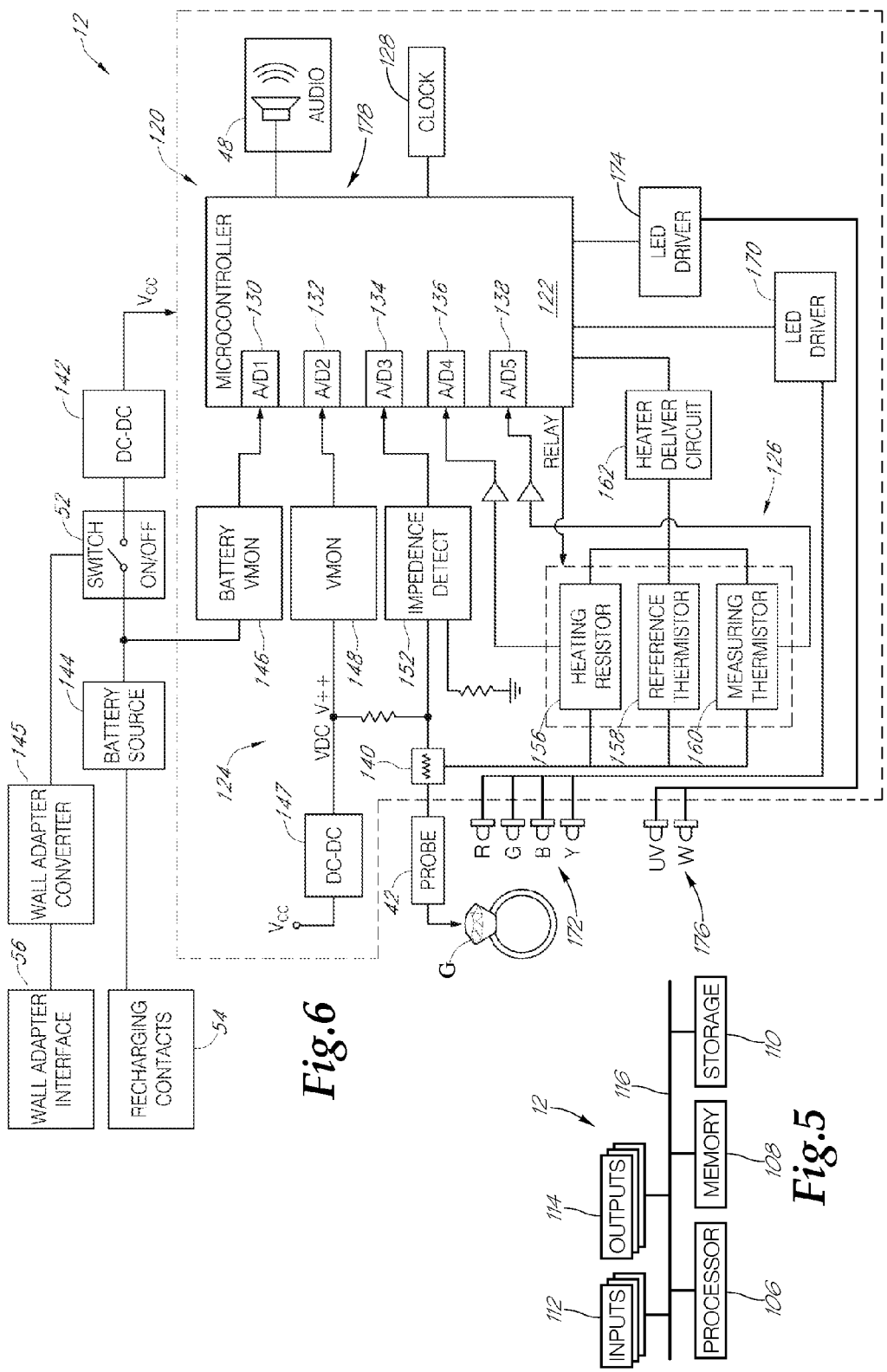

GEM TESTER

PRIORITY STATEMENT & CROSS-REFERENCE TO RELATED APPLICATIONS

This application is a continuation-in-part of U.S. patent application Ser. No. 14/301,045, entitled "Gem Tester" and filed on Jun. 10, 2014, in the name of Daniel L. Kessler et al.; which is a continuation of U.S. patent application Ser. No. 14/058,343, entitled "Gem Tester" and filed on Oct. 21, 2013, in the names of Daniel L. Kessler et al., which issued as U.S. Pat. No. 8,749,253 on Jun. 10, 2014; which is a continuation of U.S. patent application Ser. No. 13/165,053, entitled "Gem Tester" and filed on Jun. 21, 2011, in the names of Daniel L. Kessler et al., which issued on Oct. 22, 2013 as U.S. Pat. No. 8,564,316; which claims priority from U.S. Patent Application No. 61/356,943, entitled "Gem Tester" and filed on Jun. 21, 2010, in the names of Daniel L. Kessler et al.; all of which are hereby incorporated by reference for all purposes. Further, this application claims priority from U.S. Patent Application Ser. No. 61/946,521 entitled "Gem Tester" and filed on Feb. 28, 2014 in the names of Daniel L. Kessler et al., which is hereby incorporated by reference for all purposes.

TECHNICAL FIELD OF THE INVENTION

This invention relates, in general, to the identification of precious diamonds and, in particular, to gem testers for distinguishing, including identification, detection, and separation of, gems such as diamond, cubic zirconia, moissanite, white sapphire, and metals, for example, based upon physical conductivity properties.

BACKGROUND OF THE INVENTION

Gemstones such as cubic zirconium and silicon carbide, commonly known as moissanite, have become more readily available and more indistinguishable from real diamonds. As a result, the market is flooded with moissanite, which is passed off as diamond. Advances in instruments and techniques are required to authenticate diamonds and prevent fraudulent and mistaken transactions, which may occur during production and receiving jewelry for sale or repair, particularly when the received jewelry is represented as incorporating diamonds. Additionally, the electrical conductivity of moissanite is often minute, thereby making it difficult to distinguish moissanite from diamond.

SUMMARY OF THE INVENTION

It would be advantageous to achieve advances in instruments to authenticate diamonds in order to prevent fraudulent and mistaken sales. It would also be desirable to enable an electro-mechanical solution that would improve operator technique when authenticating diamonds. Further, it would be desirable to enable a physical solution that would improve the identification of moissanite. To better address one or more of these concerns, a gem tester for testing a gem under test and a horizontal recharging stand are disclosed. In one embodiment of the gem tester, a gem tester for testing a gem under test and a kit including a horizontal recharging stand are disclosed. In one embodiment of the gem tester, an elongated body has a line-of-sight contour tapering from a bulbous end to a radially deviating frontal nose having a probe extending therefrom. Internal circuitry measures electrical conductivity of the gem under test in order to identify the type of gem under test and, in one embodiment, drive a color control signal in response thereto. To enhance the identification of moissanite, a light source is disposed proximate the probe in order to expose the gem under test to ultraviolet light prior to the internal circuitry measuring electrical conductivity. Thermal conductivity may also be tested and measured. Identification of the gem under test may be made by audio or visual indication, including a voice identification by way of a speaker or other component, or a combination thereof.

In one embodiment of a gem testing kit, a horizontal recharging stand includes a base having a substantially horizontal support surface and a cavity defining a cradle within the base. The cradle is configured to securely accept the gem tester by way of an inclined support plane, opposing sidewalls, and a backstop. Electrical prongs are exposed at the backstop in order to mate with the recharging contacts when the gem tester is cradled in the horizontal recharging stand. Upon cradling, the gem tester may be recharged. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 2B is a rear perspective view of the gem tester of FIG. 1 removed from the horizontal testing stand of FIG. 1;

FIG. 2C is a bottom plan view of the gem tester of FIG. 1;

FIG. 2D is a top plan view of the horizontal testing stand of FIG. 1;

FIG. 4A is side elevation view of the gem tester of FIG. 1 in an operational embodiment testing the gem under test;

FIG. 4B is a rear elevation view of the gem tester of FIG. 4A in the operational embodiment testing the gem under test;

FIG. 5 is a functional block diagram of one embodiment of the gem tester; and

FIG. 6 is a schematic block diagram of one embodiment of the gem tester.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1:
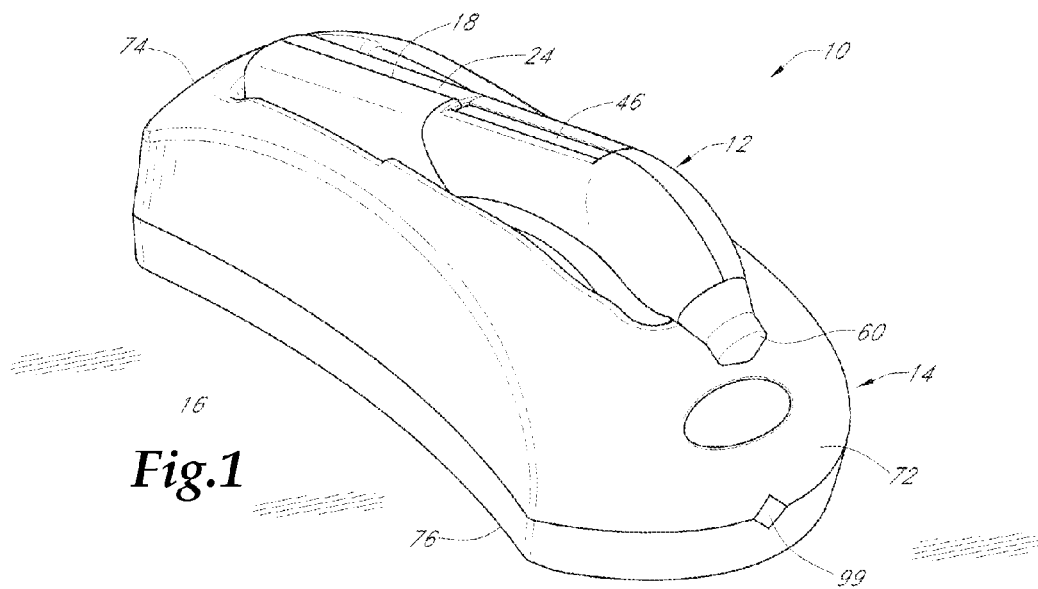
FIG. 1 is a front perspective view of one embodiment of the gem testing kit, which includes a gem tester cradled in a horizontal testing stand.
Figure 2A:
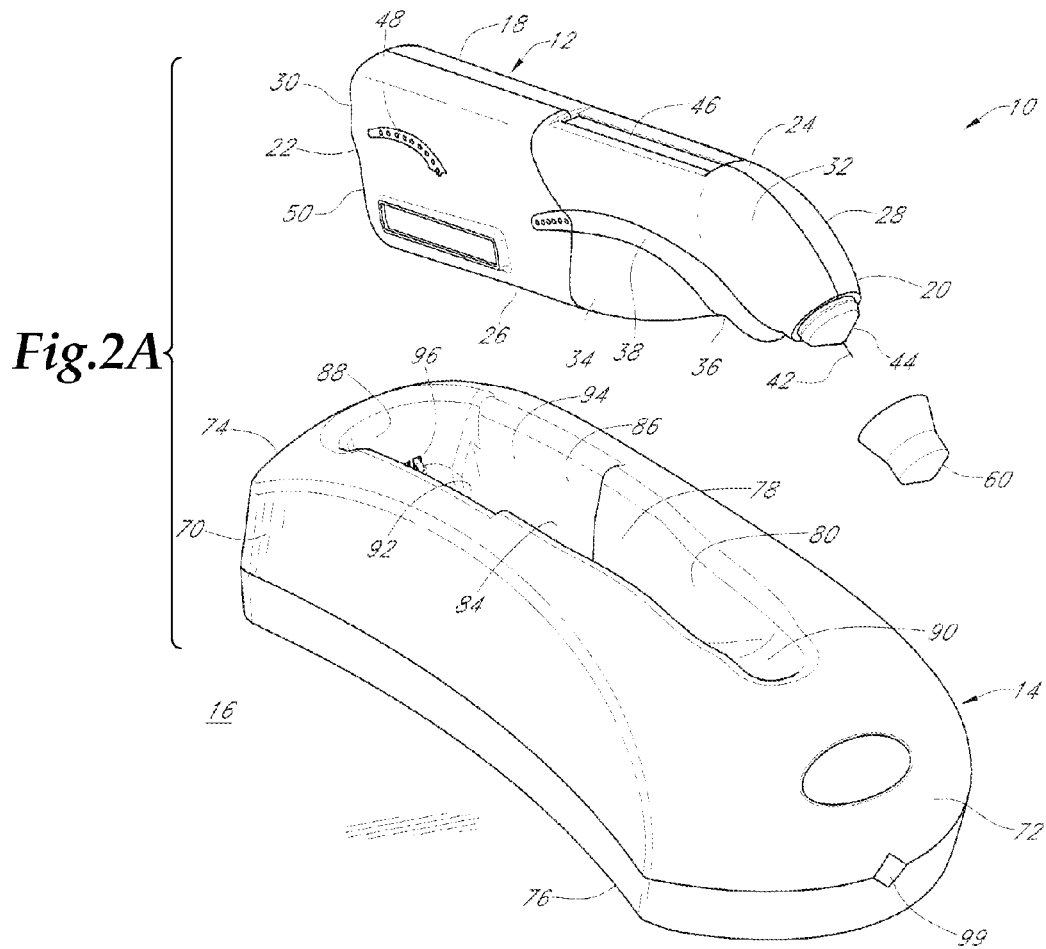
FIG. 2A is a front perspective view of the gem tester of FIG. 1 removed from the horizontal testing stand of FIG. 1.

Referring initially to FIG. 1 through FIG. 2D, therein is depicted a gem testing kit that is schematically illustrated and generally designated 10. The gem testing kit 10 includes a gem tester 12 shown cradled (See, for example, FIG. 1) within a horizontal recharging stand 14, which is depicted resting on surface 16, and removed therefrom (See, for example, FIGS. 2A and 2B). With respect to the gem tester 12, an elongated body 18 includes ends 20, 22 as well as an upper surface 24 and a lower surface 26. As the illustrated embodiment shows, the end 20 includes a radially deviating frontal nose 28 and the end 22 includes a bulbous form 30. The elongated body 18 has a tapered contour 32 from the end 22 to the end 24. A tripod-contoured surface 34 is proximate to the end 20 and configured to accept a tripod handgrip. More particularly, the tripod-contoured surface 34 furnishes a V-shape arcuate portion 36 intersecting respective lateral grip areas 38, 40.

A probe 42 for contacting a gem under test extends from the end 20. In one embodiment, the probe 42 includes a deflectable probe configured to be displaced in response to contact pressure with a gem under test. A luminescent mounting 44 is mounted proximate to the end 20 and, in the illustrated embodiment, extends from the end 20 about the probe 42 to furnish a visual indication of the gem type of the gem under test. Additionally, the luminescent mounting 44 provides an indicator light indicative of the test results and gem type (or non-gem type) by way of color. A light source 45 is also mounted proximate to the end 20 near the probe 42 to provide white illuminating light to increase visibility of the probe 42 and gem under test. Further, in one embodiment, the light source 45 emits ultraviolet light near the probe for a predetermined period of time, such as less than one second or approximately one second, in order to radiate the gem under test with ultraviolet light in order to improve the identification of moissanite. Moissanite increases electrical conductivity following stimulation by ultraviolet light. Although a particular architecture is shown for the luminescent mounting and the light source, it should be appreciated that the functionality and structure of the luminescent may be partially or fully integrated.

Display 46, which may be an LED display, is located on the upper surface 24. The LED display may be a light pipe, an LED indicator (as shown), or other type of LED display or more generally, display, for example. A speaker 48 is positioned at the end 22 and a battery compartment cover 50 is positioned on the opposite side thereto. The battery cover 50 is slidably releasable to expose a battery compartment for accepting batteries. At end 22, a switch 52 for controlling ON/OFF, recharging contacts 54, and a wall adapter interface 56 are located. In one embodiment, the wall adapter interface 56 may a universal interface capable of transmitting data and power, such as FireWire or USB. Such an interface is able to connect the gem tester 12 to an external computer, tablet, or personal communication device, for example. With this connectivity, data exchange and programming of the gem tester may occur. For example, as discussed below in further detail, the programming functionality may enable the selection of a language from multiple languages with respect to various speech support and interaction provided by the gem tester 12. With respect to the weight of the weight of the gem tester 12 in one embodiment, a center of mass 58 is proximate the end 22 when the gem tester 12 is batteried. A cone-shaped removable protective cap 60 is releasably secured with a snap-fit engagement to the end 20 to provide protection thereto over the probe 42 and luminescent mounting 44.

The horizontal recharging stand 14 includes a base 70 having a front 72 and a rear 74. A substantially horizontal support surface 76 contacts the surface 16. A cavity 78 defines a cradle 80 within the base 70. As illustrated, in one embodiment, the cradle 80 is configured to accept the gem tester 12. An inclined support plane 82 inclines from the rear 74 toward the front 72 of the horizontal recharging stand 14. Opposing sidewalls 84, 86 run the length of the inclined support plane 82 adjacent to and vertically from the inclined support plane 82. A backstop 88 located near the rear 74 of the inclined support plane 82 intersects the inclined support plane 82 and the opposing sidewalls 84, 86. Further, the inclined support plane 82 includes a tripod support crest 90 which conforms to the V-shape arcuate portion 36 of the tripod contoured surface 34 of the gem tester 12. The sidewalls 84, 86 include respective indentations 92, 94 conformed to accommodate the shape of the bulbous form 30 of the end 22.

Recharging prongs 96 extend or are exposed at the backstop 88 and are positioned to mate with the recharging contacts 54 of the gem tester 12 when the gem tester 12 is cradled within the horizontal recharging stand 14. A wall adapter interface 98 is located at the rear 74 of the horizontal recharging stand 14. Although not shown in the drawings, the recharging prongs 96 and wall adapter interface 98 are electrically coupled. Similar to the wall adapter interface 56, the wall adapter interface 98 may be a data/power interface having similar functionality. Additionally, a charging light 99, which displays the status of the recharging proximate the front 72 of the horizontal recharging stand 14 is electrically coupled to the recharging prongs 96 and wall adapter interface 98.

In operation, in a cradled configuration, the recharging stand 14 is located substantially horizontal to the surface 16. The lower surface 26 and bulbous form 30 of the end 22 of the gem tester 12 rest in contact with the sidewalls 84, 86 and the backstop 88. The slope of the inclined support plane 82 causes the end 20 to rest at a higher elevation than the end 22. The tripod support crest 90 supports the V-shape arcuate portion 36 of the tripod contoured surface 34 of the gem tester 12. In the cradled configuration, the recharging contacts 54 touch the recharging prongs 96.

When needed, the gem tester 12 may be easily drawn from the recharging stand 16 between the thumb and index finger. Then, the gem tester 12 may be presented for use by way of a one-hand tripod handgrip whereby the middle finger is placed under the V-shaped arcuate portion 36 and the thumb and forefinger are used to laterally grasp the lateral grip areas 38, 40 of the gem tester 12.

When use is complete, the gem tester 12 may be returned to the recharging stand 14 to the cradled position previously discussed. As mentioned, the center of mass 58 is proximate the end 22 when the gem tester 12 is batteried. Therefore, gravity induces the bulbous form 30 of the end 22 to fall into the cradle 80 at the backstop 88. This action results in a circuit being formed between the recharging contacts 54 of the gem tester 12 and the recharging prongs 96 of the recharging stand 14. Once cradled, the gem tester 12 has a low profile wherein the radially deviating frontal nose 28 is at the highest point.

Figure 3A:
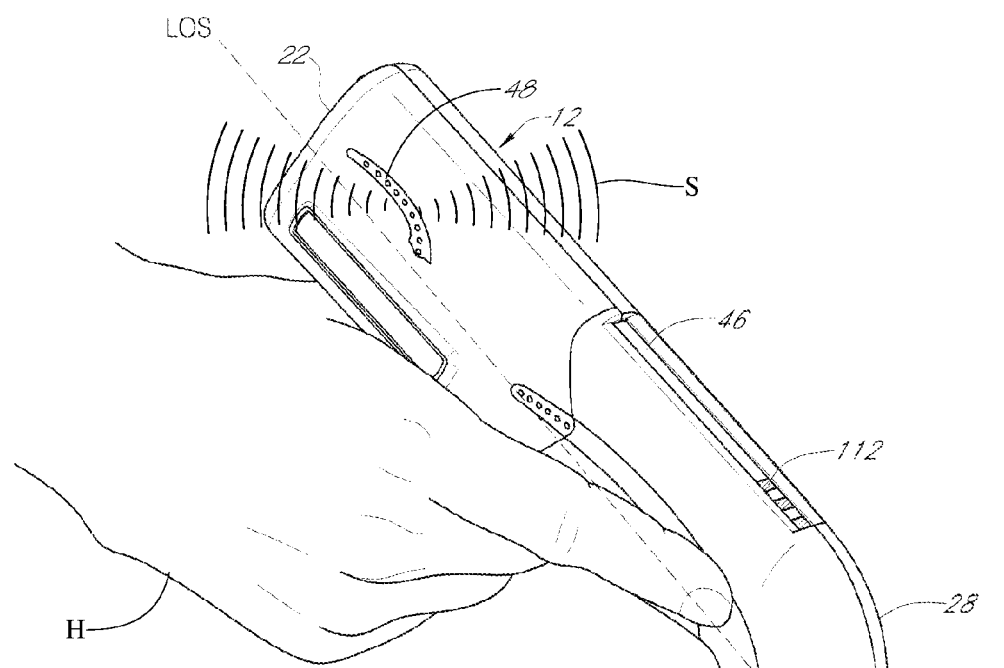
FIG. 3A is side elevation view of the gem tester of FIG. 1 in an operational embodiment preparing to test a gem under test.
Figure 3B:
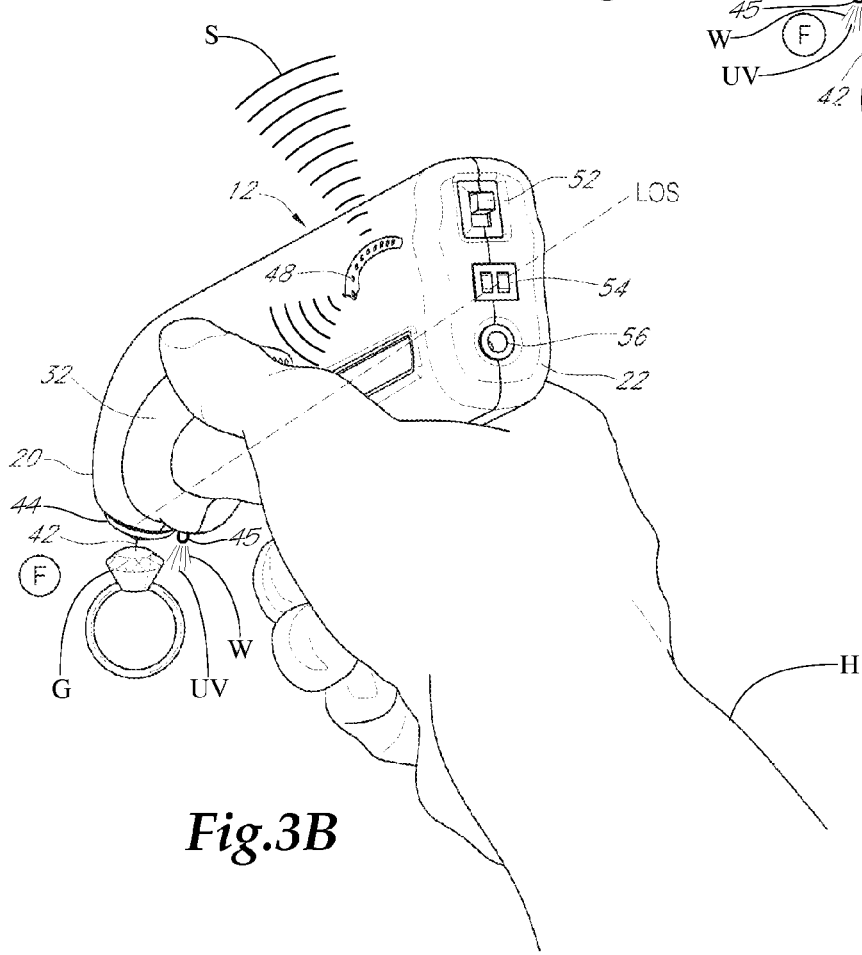
FIG. 3B is a rear elevation view of the gem tester of FIG. 3A in the operational embodiment preparing to test the gem under test.

Referring to FIGS. 3A and 3B, and describing the testing operation of the gem tester 12, the battery compartment cover 50 may be temporarily removed and replaced to install batteries, such as three AAA 1.5 V alkaline batteries or NiMH rechargeable batteries or other rechargeable batteries, for example. The switch 52 may be toggled to ON to initialize the gem tester. Following a warm-up time, which may be approximately 30 seconds, the gem tester 12 is ready to be used once the cone-shaped protective cap 60 is removed. The gem tester 12 may provide visual and/or audio indications of its readiness via the LED display 46 and the speakers 48. Using a comfortable grip, a hand H of the user holds the gem tester 12. As illustrated, the gem tester 12 may be held with a one-hand tripod hand grip by the hand H whereby the middle finger is place under the V-shape arcuate portion 36 and the thumb and forefinger are used to laterally grasp the sides of the gem tester 12 at lateral grip areas 38, 40 for handling purposes to maintain control.

Using the one-hand tripod handgrip to comfortably handle the gem tester 12, a gem under test G may be tested. The LED display 46, which may depict a bar graph 112, stops blinking and the ready light remains on when the gem tester 12 is ready for use. In one implementation, the LED display may further be utilized to select or indicate the language for the speech functionality of the gem tester 12. The user then quickly yet firmly makes contact between the probe 42 and the table of the gem under test (G). If a mounted gem is being tested, care is taken to not touch the setting. Additionally, to ensure test accuracy, the gem under test (G) and the setting should be at room temperature. A gem under test that is overheated due to prolonged exposure to the probe 42 will not test accurately. Contact is maintained for long enough to establish a reading, which in one implementation is one to two seconds. In one embodiment, prior to the reading being taken, and in one implementation, upon the detection of the deflection of the probe 42, the gem tester 12 emits ultraviolet light to stimulate the gem under test (G).

The reading process makes two measurements: thermal conductivity and electrical conductivity. The thermal conductivity test separates diamond from all known diamond simulants, except moissanite, since diamonds conduct heat significantly greater than all other gemstones, except moissanite. White sapphire is thermally conductive, yet not as conductive as diamond and moissanite and can be therefore easily being separated. Since moissanite conducts electricity in varying degrees and diamonds generally do not conduct electricity, the electrical conductivity test separates the vast majority of moissanite from diamond. As alluded, to enhance the electrical conductivity test, the gem under test (G) is radiated with ultraviolet light. Moissanite, at times, displays minimal electrical conductivity. The electrical conductivity of moissanite, however, can be increased when moissanite is exposed to ultraviolet radiation. Therefore, based upon readings from the conductivity and electrical tests, the type of gem or metal may be determined.

A line-of-sight contour 32 extends from the end 22 to the end 20 to provide a line-of-sight (LOS). This line-of-sight contour 32 allows the probe 42 and the luminescent mounting 44 to both be visible within the same field of view (F) by an operator. Further, the light source 45 illuminates the field of view (F) with, in one embodiment, both visible light (W) and ultraviolet light (UV). In this manner, the field of view (F) receives sufficient light and the operator does not have to move his or her eyes between the probe 42 and the luminescent mounting 44 during operation and determination of gem type. The operator does not want to shift his eyes away from the probe 42 to view any indicator. Often, the probe 42 is contacting a very small area and a slight movement of the probe 42 in any direction place the probe 42 into contact with a different surface resulting in a misleading reading.

Initially, in one implementation, the light source 45 may provide the white working light (W) in the field of view (F) that is visible to the operator along the line-of-sight (LOS) along the line-of-sight contour 32. That is, the light source 45 emits white working light (W) and ultraviolet light (UV) into the field of view (F) proximate the probe 42. The working light (W) illuminates the gem under test (G) to give the operator extra visibility to ensure a proper probe contact. The ultraviolet light (UV) stimulates the gem under test (G). An audio indication ($I_A$) indicates the gem tester is "ready" and a visual indication on the LED display 46 may provide further indication.

Referring now to FIGS. 4A and 4B, based upon readings from the conductivity and electrical tests, the type of gem or metal may be determined by the gem tester 12. Following the determination, the luminescent mounting 44 provides a color visual indication ($I_V$), which is in the field of view (F) and visible along the line-of-sight (LOS) along the line-of-sight contour 32. Moreover, the speakers 48 may provide an audio indication ($I_A$) by way of a voice to indicate the type of gem detected. As discussed further below, the audio indications ($I_A$) provided may also relate to the status of gem tester 12. For example, with respect to the visual indication ($I_V$), a green light (G) may indicate diamond, a blue light (B) may indicate moissanite, and a yellow light (Y) may indicate white sapphire, and a red light (R) may indicate metal.

Referring now to FIG. 5, the gem tester 12 is depicted as a computing device which includes a processor 106, memory 108, storage 110, various inputs 112, and various outputs 114 interconnected with various buses 116 in a common or distributed, for example, mounting architecture. In other implementations, in the computing device, multiple processors and/or multiple buses may be used, as appropriate, along with multiple memories and types of memory. The processor 106 may process instructions for execution within the computing device, including instructions stored in the memory 108 or in storage 110. The memory 108 stores information within the computing device. In one implementation, the memory 108 is a volatile memory unit or units. In another implementation, the memory 108 is a non-volatile memory unit or units. Storage 110 provides capacity of providing mass storage for the computing device. Various inputs 112 and outputs 114 provide connections to and from the computing device, wherein the inputs 112 are the signals or data received by the computing device, and the outputs 114 are the signals or data sent from the gem tester 12.

The memory 108 and storage 110 are accessible to the processor 106 and include processor-executable instructions that, when executed, cause the processor 106 to execute a series of operations. The processor-executable instructions measure electrical conductivity of the gem under test, responsive to the light source emitting ultraviolet light into the field of view, in order to identify the type of gem under test. Further, the processor-executable instructions measure thermal conductivity to identify the gem under test. Additionally, in one embodiment, the processor-executable instructions provide visual and audio indications of the status of the gem tester in one of many languages, such as English, Spanish, Japanese, German, French, Russian, Korean, etc. The visual indications of the status and gem type may be found on the LED display and the audio indications may be sourced from the speakers. The visual and audio indications relate to status of the gem tester, such as "warming up," "ready," and "low battery," for example. The gem type indications relate to the result of the testing and include "diamond," "white sapphire," "cubic zirconia," "moissanite," and "metal," for example.

FIG. 6 depicts one embodiment of the gem tester 12 in further detail. A circuit portion 120, including the microcontroller, which may be a microprocessor 122 or other configuration of a processor 106, memory 108, and storage 110 as presented in FIG. 5, is located communicatively with circuit portions 124, 126 and configured to determine or more generally identify verified—or, more generally, identified—type and drive a color control signal in response thereto. The identified type being selected from a plurality of gem types including at least three materials. Additionally, the identified type may be a non-gem type, such as metal. More particularly, at the center of the circuit portion 120, the microprocessor 122, operating under the frequency source of a clock 128, processes a number of analog voltages at inputs 130, 132, 134, 136, 138 to produce a number of outputs (discussed below) indicative of whether a measurement for the gem under test (G) is within a specific range indicating that the gem under test is diamond, moissanite, or other metal.

The switch 52, which may be a single pole single throw mechanical switch, controls the ON/OFF state of gem tester 12 and the application of voltage to DC-DC converter 142. A voltage source may be a battery source 144, regular or rechargeable, or wall power provided by a wall adapter converter 145 and wall adapter interface 56. The low voltage DC-DC converter 142 converts the battery source 144 or voltage supplied by the wall adapter converter 145 to an acceptable voltage for powering analog and digital circuitry. A battery voltage monitor 146 is provided to detect a low voltage condition in the battery source and communicate this information to the microprocessor 122 via the input 132. A DC-DC converter 147 and a monitor circuit 148 are designed to condition the signal for processing within the microprocessor 122. If low voltage condition is detected, the audio speaker 48 or the visual display 46, both of which are connected to the microprocessor 122, may provide an indication of faulty voltage while the gem tester 12 temporarily suspends testing. In particular, the microprocessor 122 discontinues gem testing when the voltage source input is below a certain pre-determined threshold.

The circuit portion 124 is electrically coupled to the probe 42, which is shown as a deflectable probe having a spring 140 thereat, to measure electrical conductivity of the gem under test 110. More particularly, the circuit portion 124 includes electrical components 150, including the DC-DC converter 147, the voltage monitor 148, and an impedance detector 152, for applying and sampling a voltage across the gem under test (G). The electrical components 150 successively sample the voltage across the gem under test (G) to provide data for determining a gem type based upon a predetermined number of samples exceeding a threshold voltage. As shown, the voltage monitor is coupled to the microprocessor 122 by the input 132 and the impedance detector 152 is coupled to the microprocessor by the input 134. In one embodiment, in order to improve the measurement and identification of moissanite, the circuit portion 124 is coupled to the probe 42 to measure, responsive to the light source 45 emitting the ultraviolet light (UV) into the field of view (F), electrical conductivity of the gem under test (G). In this embodiment, the microprocessor coordinates the emission of the ultraviolet light (UV) and subsequent electrical conductivity testing of the gem under test (G).

The circuit portion 126 is thermally coupled to the probe 42 to measure thermal conductivity of the gem under test 110. Heating components 154, including a heating resistor 156, reference thermistor 158, and a measuring thermistor 160, heat the probe 42 and monitor the temperature of the heated probe 42. The heater deliver circuit 162 is located between the microprocessor 122 and the heating resistor 156, the reference thermistor 158, and the measuring thermistor 160. As depicted, the heating resistor 156 is connected to the microprocessor 122 by the input 136 and an amplifier. Similarly, the measuring thermistor 160 is connected to the microprocessor 122 by the input 138 and an amplifier.

An LED driver 170 controls LEDs 172 in response to receiving signals from the microprocessor 172. In one implementation, the LEDs provide indication lights that indicate the composition of the gem under test. For example, a green light (G) may indicate diamond, a blue light (B) may indicate moissanite, a yellow light (Y) may indicate white sapphire, and a red light (R) may indicate metal. That is, in the illustrated embodiment, the LED driver 170 and LEDs 172 provide at least three colors of light, which are indicators of three separate types of gem or non-gem materials. Similarly, a driver 174 and LEDs 176 provide a white working light (W) and an ultraviolet light (UV) for exposing the gem under test (G) to ultraviolet light (UV) for a minimum amount of time (e.g., less than or equal to one second) to increase electrical conductivity in the instance of moissanite. It should be appreciated that the drivers 170, 174 may be partially or fully integrated. Additionally, the LED functionality may be partially or fully integrated.

A circuit portion 176 may include the microcontroller 122 and the speaker 48. The circuit portion 176 is configured to provide a verbal indication of the gem tester status and gem type in a selectable plurality of languages. The audio indications relate to status of the gem tester, such as "warming up," "ready," and "low battery," for example. Also, gem type indications are provided relative to the result of the testing and include "diamond," "white sapphire," "cubic zirconia," "moissanite," and "metal," for example.

It should be appreciated that the circuit design and architecture depicted in FIG. 6 is only exemplary and illustrative. Other designs and architectures are within the teachings presented herein. By way of example, the circuit portion 124 configured to measure electrical conductivity and the circuit portion 126 configured to measure thermal conductivity may be combined as other circuit portions may be partially or fully integrated. By way of further example, illumination or indicators other than LEDs may be utilized to provide working light and color indicators.

The order of execution or performance of the methods, instruction, and data flows illustrated and described herein is not essential, unless otherwise specified. That is, elements of the methods, instructions, and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention will be apparent to persons skilled in the art upon reference to the description. It is, therefore, intended that the appended claims encompass any such modifications or embodiments.

What is claimed is:

1. A gem tester for testing a gem under test, the gem tester comprising:
    an elongated body having a first end and a second end;
    a probe extending from the first end of the elongated body and contacting a field of view proximate the probe;
    a light source disposed at the first end of the elongated body, the light source emitting ultraviolet light into the field of view proximate the probe;
    an electrical conductivity circuit portion located within the elongated body, the electrical conductivity circuit portion being electrically coupled to the probe to measure, responsive to the light source emitting the ultraviolet light into the field of view, electrical conductivity of the gem under test;
    an identification circuit portion located within the elongated body communicatively with the electrical conductivity circuit portion, the identification circuit portion configured to determine identified type and drive a control signal in response thereto, the identified type being selected from a plurality of gem types; and
a line-of-sight contour extending from the second end of the elongated body to the first end of the body, including the field of view proximate the probe.

2. The gem tester as recited in claim 1, further comprising a speech circuit portion coupled to the electrical conductivity circuit portion and the identification circuit portion, the speech circuit portion configured to provide a verbal indication of the gem tester status and gem type in a selectable plurality of languages.

3. The gem tester as recited in claim 2, wherein the speech circuit portion further comprises a microprocessor and a speaker.

4. The gem tester as recited in claim 1, further comprising a thermal conductivity circuit portion located within the elongated body, the thermal conductivity portion being thermally coupled to the probe to measure thermal conductivity of the gem under test.

5. The gem tester as recited in claim 4, wherein the thermal conductivity circuit portion further comprises heating components for heating the probe and monitoring the temperature of the heated probe.

6. The gem tester as recited in claim 4, further comprising a luminescent mounting extending from the first end communicatively with the indication circuit portion, the luminescent mounting providing a plurality of colors corresponding to the plurality of gem types, the luminescent mounting lighting one of the plurality of colors in response to receiving the color control signal.

7. The gem tester as recited in claim 6, wherein the luminescent mounting further comprises green, red, yellow and blue colors.

8. The gem tester as recited in claim 1, wherein the elongated body further comprises:
the first end having a radially deviating frontal nose;
the second end having a bulbous form;
the elongated body being tapered from the first end to the second end; and
a center of mass being proximate the second end when the gem tester is batteried.

9. The gem tester as recited in claim 1, wherein the elongated body further comprises a tripod contoured surface proximate to the first end, the tripod contoured surface configured to accept a tripod hand grip.

10. The gem tester as recited in claim 1, wherein the probe further comprises a deflectable probe configured to be displaced in response to contact pressure.

11. The gem tester as recited in claim 1, wherein the electrical conductivity circuit portion further comprises electrical components for applying a voltage across the gem under test, the electrical components successively sampling the voltage across the gem under test to provide data for determining a gem type based upon a predetermined number of samples exceeding a threshold voltage.

12. The gem tester as recited in claim 1, wherein the identification circuit portion further comprises a microprocessor.

13. The gem tester as recited in claim 1, wherein the electrical conductivity circuit portion and identification circuit portion are at least partially integrated.

14. The gem tester as recited in claim 1, wherein the identification circuit portion and the speech circuit portion are at least partially integrated.

15. The gem tester as recited in claim 1, wherein the light source emits white light source to illuminate the gem under test.

16. The gem tester as recited in claim 1, wherein the gem tester identifies diamond, metal, white sapphire, and moissanite.

17. The gem tester as recited in claim 1, further comprising a releasable cap having a snap-fit engagement about the probe.

18. A gem tester for testing a gem under test, the gem tester comprising:
an elongated body having a first end and a second end;
a probe extending from the first end of the elongated body and contacting a field of view proximate the probe;
a light source disposed at the first end of the elongated body, the light source emitting ultraviolet light into the field of view proximate the probe;
a first circuit portion located within the elongated body, the first circuit portion being electrically coupled to the probe to measure electrical conductivity of the gem under test;
a second circuit portion located within the elongated body, the second circuit portion being thermally coupled to the probe to measure thermal conductivity of the gem under test;
a third circuit portion located within the elongated body communicatively with the first and second circuit portions, the third circuit portion configured to determine identified type and drive a color control signal in response thereto, the identified type being selected from a plurality of gem types;
a fourth circuit portion coupled to the third circuit portion, the fourth circuit portion configured to provide a verbal indication of the gem tester status and gem type in a selectable plurality of languages;
a luminescent mounting mounted proximate to the first end and communicatively with the third circuit portion, the luminescent mounting providing a plurality of colors corresponding to the plurality of gem types, the luminescent mounting lighting one of the plurality of colors in response to receiving the color control signal; and
a line-of-sight contour extending from the second end of the elongated body to the first end of the body, including the luminescent mounting at the probe and the field of view proximate the probe.

19. The gem tester as recited in claim 18, wherein the elongated body further comprises:
the first end having a radially deviating frontal nose;
the second end having a bulbous form;
the elongated body being tapered from the first end to the second end; and
a center of mass being proximate the second end when the gem tester is batteried.

20. A gem testing kit, comprising, in combination:
a gem tester comprising:
an elongated body having a line-of-sight contour tapering from a bulbous end to a radially deviating frontal nose having a probe extending therefrom,
a light source disposed at the radially deviating frontal nose, the light source emitting ultraviolet light into a field of view proximate the probe;
a center of mass proximate the bulbous end when the gem tester is batteried,
recharging contacts exposed at the bulbous end,
an internal circuit coupled to the contact and the recharging contacts, the internal circuit configured to measure electrical conductivity of the gem under test, responsive to the light source emitting ultraviolet light into the field of view, in order to identify the type of gem under test; and a horizontal recharging stand comprising:
- a base having a substantially horizontal support surface,
- a cavity defining a cradle within the base, the cradle configured to accept the gem tester, the cradle including an inclined support plane, opposing sidewalls and a backstop, and
- recharging prongs are exposed at the backstop, the electrical prongs being positioned to mate with the recharging contacts when the gem tester is cradled within the horizontal recharging stand.

\* \* \* \* \*